US00RE36629E

United States Patent [19]

Zaslavsky et al.

[11] E Patent Number: Re. 36,629

[45] Reissued Date of Patent: Mar. 28, 2000

[54] MULTIPLE LIGATING BAND DISPENSER

[75] Inventors: Ella Zaslavsky, Marblehead; Joshua Tolkoff, Brookline; Fernando Alvarez de Toledo, Concord; Douglas L. Horka, Northboro, all of Mass.

[73] Assignee: Boston Scientific Corporation, Watertown, Mass.

[21] Appl. No.: 08/820,866

[22] Filed: Mar. 20, 1997

Related U.S. Patent Documents

Reissue of:

[64] Patent No.: 5,398,844
Issued: Mar. 21, 1995
Appl. No.: 08/189,236
Filed: Jan. 31, 1994

[51] Int. Cl.[7] ..... B23Q 7/04

[52] U.S. Cl. ..... 221/208; 606/140; 128/831

[58] Field of Search ..... 221/208, 255, 221/262, 185, 268, 112, 224; 606/140, 141, 135; 128/831

[56] References Cited

U.S. PATENT DOCUMENTS

| | | | |
|---|---|---|---|
| 2,737,181 | 3/1956 | Beard | 606/140 |
| 3,687,138 | 8/1972 | Jarvik | 128/322 |
| 3,760,810 | 9/1973 | Van Hoorn | 606/140 |
| 3,870,048 | 3/1975 | Yoon | 606/141 |
| 4,085,743 | 4/1978 | Yoon | 128/6 |
| 4,103,680 | 8/1978 | Yoon | 128/6 |
| 4,257,419 | 3/1981 | Geltner et al. | 606/140 |
| 4,374,523 | 2/1983 | Yoon | 128/326 |
| 4,548,201 | 10/1985 | Yoon | 128/326 |
| 4,735,194 | 4/1988 | Stiegmann | 600/104 |
| 4,794,927 | 1/1989 | Yoon | 128/326 |
| 4,990,152 | 2/1991 | Yoon | 606/140 |
| 5,122,149 | 6/1992 | Broome | 606/140 |
| 5,203,863 | 4/1993 | Bidoia | 606/140 |
| 5,236,434 | 8/1993 | Callicrate | 606/135 |
| 5,269,789 | 12/1993 | Chin et al. | 606/140 |
| 5,320,630 | 6/1994 | Ahmed | 606/140 |
| 5,425,736 | 6/1995 | Wadsworth | 606/135 |
| 5,507,797 | 4/1996 | Suzuki et al. | 606/140 |
| 5,569,268 | 10/1996 | Hosoda | 606/140 |

*Primary Examiner*—Kenneth W. Noland
*Attorney, Agent, or Firm*—Kenyon & Kenyon

[57] ABSTRACT

Apparatus for dispensing a plurality of ligating bands individually and sequentially. A support, attached to the distal end of an endoscope, carries the plurality of ligating bands at axially spaced positions along an exterior surface. The distal ends of each set of independent displacement filaments each ligating band releasably attach to the distal edge of the dispenser. Each filament loops around the corresponding ligating band and returns past the distal edge of the dispenser and through the endoscope to the proximal end thereof. When a physician pulls a set of filaments proximally, the loop in each filament advances the corresponding ligating band off the distal edge of the dispenser.

41 Claims, 3 Drawing Sheets

MULTIPLE LIGATING BAND DISPENSER

Matter enclosed in heavy brackets [ ] appears in the original patent but forms no part of this reissue specification; matter printed in italics indicates the additions made by reissue.

BACKGROUND OF THE INVENTION

1. Field of the Invention

This invention generally relates to ligating instruments and more particularly to instruments capable of dispensing ligating bands in a sequential manner.

2. Description of Related Art

It is well known that one can treat various types of lesions including internal hemorrhoids by ligation. The object of ligation is to position an elastic cord, or ligating band, at the lesion to stop circulation through tissue and allow the tissue to die whereupon the body sloughs off the dead tissue.

The following U.S. Pat. Nos. disclose various embodiments of ligating instruments:

U.S. Pat. No. 3,760,810 (1973) Van Hoorn

U.S. Pat. No. 4,257,419 (1981) Göltner et al.

U.S. Pat. No. 4,735,194 (1988) Stiegmann

U.S. Pat. No. 5,269,789 (1993) Chin et al.

U.S. Pat. No. 3,760,810 to Van Hoorn discloses an instrument for facilitating the placement of a single ligating band or set of bands. The instrument includes, at its distal end, a ligating band dispenser comprising two rigid, concentric tubes. The tubes can slide with respect to each other under the control of a trigger mechanism at the proximal end of the instrument. A rigid endoscope having internal passages forming a suction path and a light path interconnect the trigger mechanism and dispenser. The inner tube can be loaded with a set of one or more elastic rings or ligating bands. A separate stopper bar attaches to the instrument to prevent premature dispensing. When the instrument is located proximate a lesion, a surgeon removes the stopper bar and applies vacuum to draw tissue into a hollow passage at the distal end of the instrument. Pulling on the trigger retracts the inner tube. A radial surface or shoulder on the outer tube engages the ligating band so it can not displace with the inner tube. As the inner tube is withdrawn from the ligating band, it collapses onto the tissue.

U.S. Pat. No. 4,257,419 to Göltner et al discloses a rigid endoscope that includes a ligating band dispenser with an inner tube that moves with respect to an outer tube to dispense a ligating band. This dispenser is oriented at right angles to the rigid endoscope and includes a structure for moving the inner tube of the dispenser in this configuration.

U.S. Pat. No. 4,735,194 to Stiegmann discloses a flexible endoscope ligating instrument in which a flexible endoscope structure includes a biopsy channel and a suction channel extending between the proximal and distal ends. A dispenser, like the dispenser structure shown in the Van Hoorn and G öltner patents, includes an inner tube that moves axially with respect to an outer tube at the distal end of the instrument. The outer tube connects to the distal end of the endoscope. An operating mechanism in the form of a pull wire with a weighted handle maintains tension on the inner tube so it does not displace axially outward while the instrument is being positioned. For some applications it is suggested that the endoscope structure be inserted through an overtube to prevent premature dispensing. Suction can be applied to draw tissue into a central aperture of the dispenser. Then a surgeon pulls the handle and retracts the inner tube axially past the distal end of the outer tube to force the ligating band off the instrument onto the tissue.

Each of the foregoing instruments dispenses a single ligating band or a single set of ligating bands at a single location. None of the patents suggests dispensing ligating bands at discrete locations. The Van Hoorn patent does disclose the possibility of depositing plural ligating bands. However, Van Hoorn seems only to suggest dispensing plural ligating bands at a single site in a single operation. The apparatus disclosed in the Van Hoorn, Göltner or Stiegmann patents apparently would have to rely on a surgeon's sense of touch in order to displace the inner tube by an incremental distance corresponding to the thickness of a stretched ligating band to deposit a plurality of bands at different sites. That would be very difficult to accomplish.

Indeed, when it was desired to deposit ligating bands at different sites, the common practice was to withdraw the entire instrument from the patient and load a new ligating band onto the inner tube. Loading ligating bands on an instrument requires special tools and can be time consuming particularly if the special tooling must be retrieved to install each ligating band individually while the instrument is withdrawn. Each of these instruments requires some structure, such as special stoppers or overtubes, for preventing the premature dispensing of the ligating band. Consequently, none of these instruments is readily adapted for dispensing ligating bands at different sites without withdrawing the instrument after each individual site is ligated.

U.S. Pat. No. 5,269,789 to Chin et al, which is assigned to the same assignee as this invention, discloses a multiple ligating band dispenser for ligating instruments. Interfitted inner and outer structures support a plurality of ligating bands at axially spaced locations. Retraction of the inner structure dispenses one ligating band. Extension of the inner structure advances remaining ligating bands distally and axially so a next retraction dispenses another ligating band. This ligating band dispenser over comes many, but not all, of the undesirable characteristics of single-band dispensers. For example, prior art single-band dispensers can eject a ligating band inadvertently if, during placement, tissue at the distal end of the dispenser, rather than the physician moves the distal edge of the movable tube. The multiple band dispenser over comes this problem by using a spring to bias the movable tube to a distal position. However, the use of the spring increases the force that must be used during the dispensing operation. Also, the distal edge of the movable tube is the most distal part of the dispenser. During placement, this edge engages the lesion to form a vacuum seal thereby to allow the lesion to be withdrawn into the lumen of the endoscope. When the movable tube moves proximally during the dispensing operation, the vacuum seal can break thereby enabling the lesion to pull away from the dispenser.

SUMMARY

Therefore it is an object of this invention to provide an instrument that can dispense plural ligating bands in sequence at discrete sites.

Another object of this invention is to provide a ligating instrument that can deposit plural ligating bands in sequence without requiring the instrument to be removed from a patient after each ligation.

Still another object of this invention is to provide a ligating band dispenser for attachment to diverse introducer structures including rigid and flexible endoscopes for ligating tissue.

Still another object of this invention is to provide a dispenser for attachment to a ligating instrument that dispenses plural ligating bands at different locations, that is reliable and easy to use and that inherently prevents any premature dispensing of the ligating band during instrument positioning.

Yet still another object of this invention is to provide a dispenser for attachment to a ligating instrument that dispenses plural ligating bands at different locations, that is reliable and easy to use and that minimizes the possibility of breaking a vacuum seal between the distal end of the instrument and a lesion being treated.

In accordance with one embodiment of this invention, a ligating band dispenser attaches to the distal end of an endoscopic device characterized by a lumen extending between its proximal and distal ends. The dispenser includes a support that attaches to the distal end of the endoscopic device and that carries a given plurality of ligating bands. The support has a passage therethrough for communication with the lumen in the endoscope. The dispenser further includes a plurality of independent displacement structures corresponding to the given plurality extending into the lumen of the endoscopic device. Each such displacement structure attaches to the support and engages a corresponding one of the ligating bands. An operating portion extends from each independent displacement structure through the lumen of the endoscopic device whereby proximal motion of an operating portion from the proximal end of the endoscopic device transfers the most distal ligating band off the distal end of the support.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
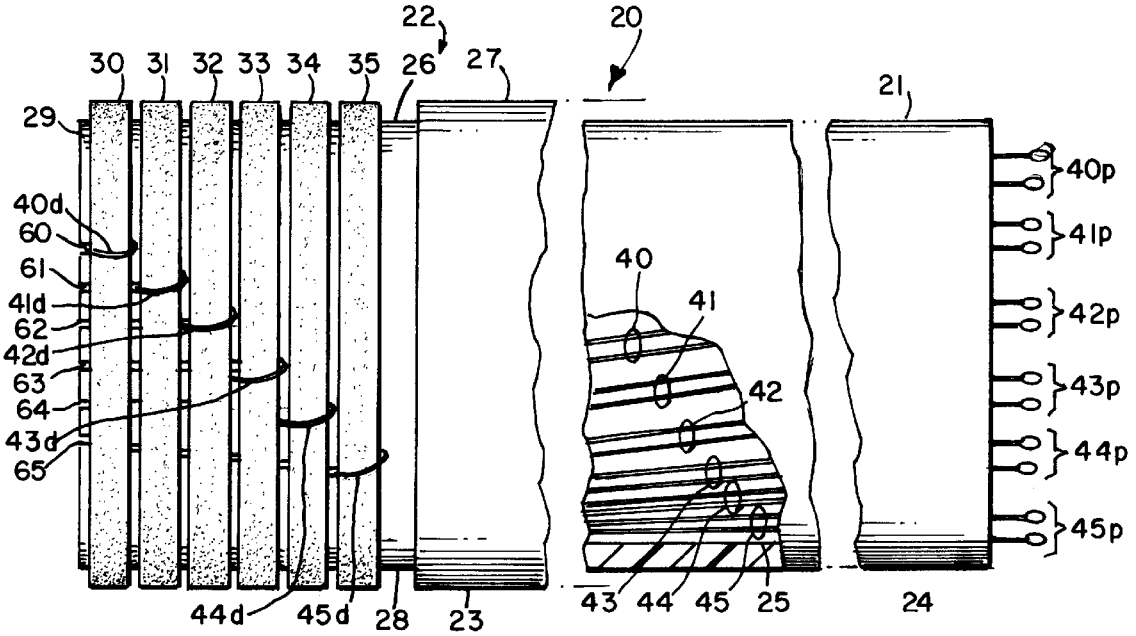
FIG. 1 depicts one embodiment of a ligating instrument including a multiple ligating band dispenser constructed in accordance with this invention.

In FIG. 1 a ligating instrument 20 constructed in accordance with this invention includes an endoscope 21 and a dispenser 22. The endoscope 21 extends between a distal end 23 and a proximal end 24 and includes a lumen 25. The dispenser 22 includes a support 26 that attaches to the distal end 23 of the endoscope 21 by means of a connector 27.

An outer surface 28 that is, in this particular embodiment, cylindrical in shape carries a plurality of ligating bands in a stretched condition proximally of a distal edge 29. In this particular embodiment and for purposes of discussion, the support 26 carries six ligating bands 30 through 35 on the surface 28.

A plurality of independent displacement structures in the form of filaments 40 and 45 have distal end portions 40d through 45d that engage the corresponding ligating bands 30 through 35. Individual, proximal operating portions 40p through 45p emerge from the proximal end of the endoscope 21. Manipulation of the operating portions 40p through 45p in the succession 40p, 41p, 42p, 43p, 44p and 45p sequentially displace and dispense the ligating bands in the order 30, 31, 32, 33, 34 and 35.

In use, a physician will attach a dispenser 22 to the distal end 23 of a rigid or flexible endoscope 21 or other introducing means. When the distal edge 29 is positioned against a lesion, the physician will apply suction to the lumen 25 thereby to move the lesion into the support 26 toward the lumen 25. Next the physician pulls the operating portions 40p proximally so the distal portions 40d, by virtue of their routing and attachment at the distal end 29 of the support 26, displace the ligating band 30 distally (to the left in FIG. 1). When the band 30 clears the distal edge 29 it collapses onto the lesion. If another lesion is to be ligated, the physician positions the distal edge 29 at that lesion and withdraws the operating portions 41p to dispense the ligating band 31.

FIGS. 2 through 5 depict one embodiment of a support 26 used in the dispenser 22. This support includes a central cylindrical body portion 50 about a central lumen 51 that aligns with the lumen 25. A reduced radius shoulder 52 extends proximally from the central body portion 50. The exterior cylindrical surface 28 terminates at an axial lip 54 that forms the distal edge 29.

Figure 2:
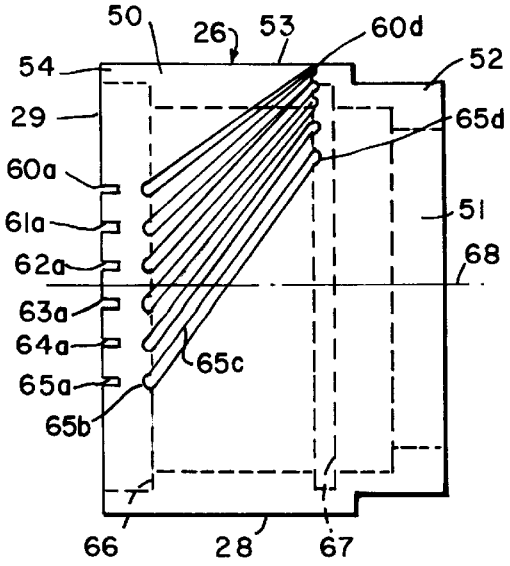
FIGS. 2 through 5 are views of a support used in the dispenser of FIG. 1.
Figure 3:
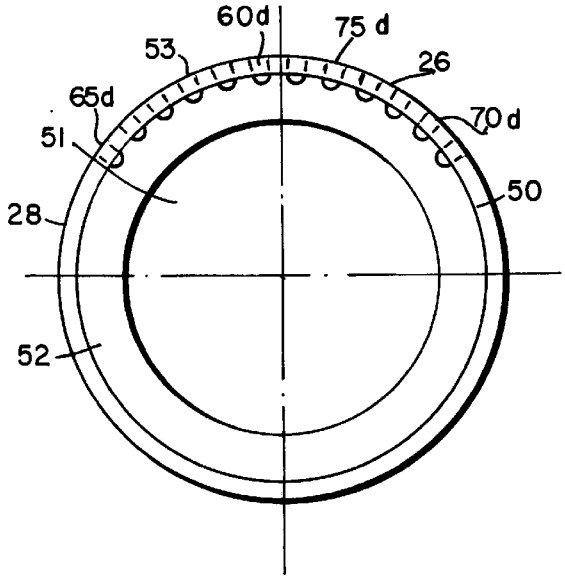
Figure 4:
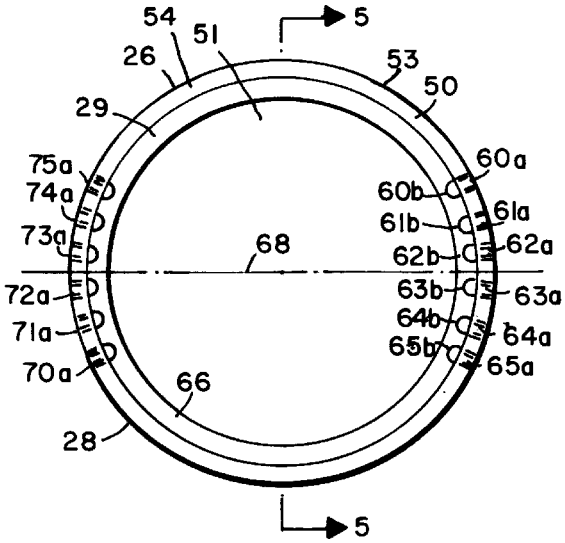
Figure 5:
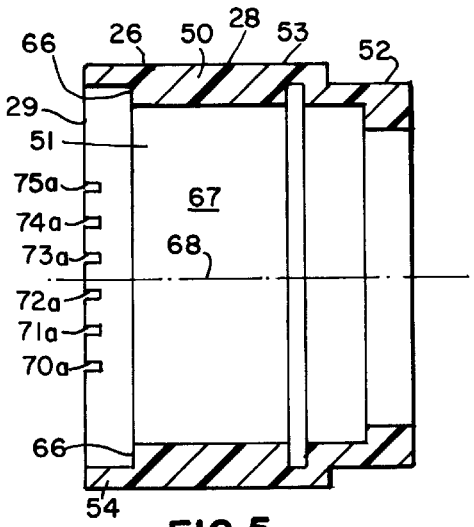

As shown particularly in FIGS. 2 through 4, the support 26 also includes a plurality of guideways 60 through 65 starting with a plurality of axially extending notches 60a through 65a formed in the distal edge 29. In order to keep the lumen 51 and the distal end of the lumen 25 clear of any filaments 40 that might interfere with the orderly transfer of a lesion into the lumen 51, the support 26 additionally include a series of passages 60b through 65b through a radial wall 66 from the interior of the support 26 to a series of grooves 60c through 65c formed in the exterior surface 28. Passages 60d through 65d exit into the lumen 51 through an internal circumferential channel 67 formed adjacent the shoulder 52. Normally the channel 67 will be located proximally of any lesion during ligation.

In this specific embodiment, the axially extending notches 60a through 65a are closely spaced along one portion of the distal edge 29. Passages 60d through 65d are located closely adjacent to each other and are displaced essentially 90° about an axis 68 through the support 26.

In the specifically disclosed dispenser, each independent displacement structure comprises a pair of filaments. Other numbers of filaments could also be utilized on each displacement structure. When, however, each structure includes a pair of filaments, a second set of guideways 70 through 75 are arranged with notches 70a through 75a at the distal edge 29 being disposed oppositely to notches 60a through 65a respectively. Passages 70d through 75d are also displaced approximately 90° angularly with respect to the passages 70a through 75a so that all the passages 60d through 65d and 70d through 75d are closely spaced at the internal channel 67.

Figure 6:
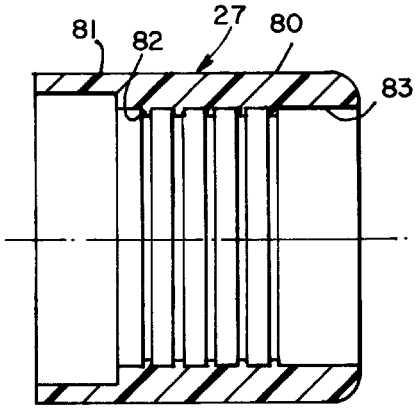
FIG. 6 is a view of an adapter used in the dispenser of FIG. 1.

Now referring to FIGS. 1 and 6, the connector 27 has a tubular body 80 with a distally extending cylindrical lip 81 that engages the shoulder 52 on the support 26. The connector 27 and support 26 may be joined by ultrasonic, welding, adhesives, other joining techniques or by friction.

The main portion of the body 80 extends proximally from the cylindrical lip 81 to overlie and releasably to engage the distal end of the endoscope 21 to allow an exchange of dispensers 22. Spaced, radially extending, cylindrical ribs 82 on an inner surface 83 enhance the engagement between the connector 27 and the endoscope 27.

Figure 7:
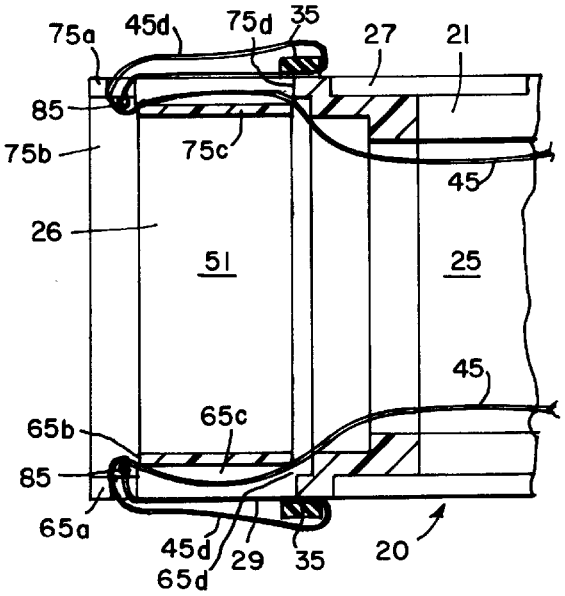
FIG. 7 is a view, in cross section, of the distal end of a ligating instrument, particularly the dispenser shown in FIG. 1 with one routing of filaments used to displace ligating bands.

FIG. 7 depicts, in a simplified form, a dispenser 22 with a single ligating band 35 remaining on the support surface 28. Filaments 45 constitute the independent displacement means for the ligating band 35. Distal portions 45d are essentially at diametrically opposed positions of the support 26. An end 85 on each of the distal portions 45d lies in one of the corresponding, diametrically opposed notches 65a and 75a. As both filaments 45 follow analogous paths through their respective guideways 65 and 75, the following discussion is limited to the upper filament 45 at the top of FIG. 7 in the guideway 75. From the notch 75a, the filament distal portion 45d extends along the surface 28 and under the ligating band 35 and any other distally located ligating bands. The filament 45 then loops around the proximal end of the ligating band 35 and returns, again under any distal ligating bands and to the notch 75a. Next the filament 45 extends through the passage 75b, a groove 75c, and passage 75d to isolate the filament 45 from the lumen 51. After passing through the passage 75d the filament distal portion 45d passes into the lumen 25 of the endoscope 21. Thus in this particular embodiment, the independent displacement means for the ligating band 35 comprises the distal portions 45d of a pair of filaments 45 that engage the corresponding ligating band 35.

Figure 7A:
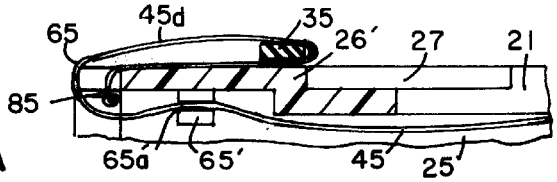
FIG. 7A is a view of a portion of the distal end of the ligating instrument in FIG. 7 modified to provide an alternative filament routing.

FIG. 7A depicts an alternative construction for a dispenser 26' that substitutes inwardly, axially extending guideways for the guideways 60 through 65. In FIG. 7A, this internal guideway comprises a radial member 65' having an axially extending passage 65a' formed therethrough. The passage 65a' could include radially and tangentially extending portions thereby to form an L-shaped slot to facilitate the introduction of the filaments into their respective passages. This structure will, like the structure in FIG. 7, keep each filament next to the inside wall of the lumen 25. Each guideway, such as guideway 65', can be angularly spaced with respect to a corresponding notch, such as notch 65a, in order to provide an angular translation corresponding to the angular translation the grooves in FIG. 7 provide.

Figure 8:
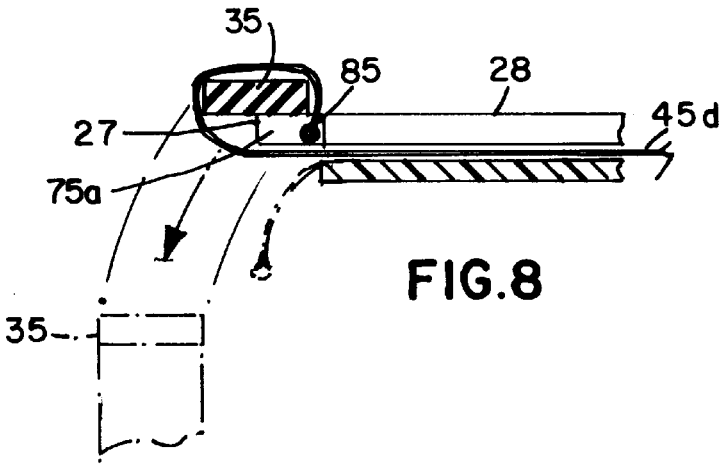
FIG. 8 is a view, in cross section, of a portion of a dispenser shown in FIG. 1.

Once a physician begins to translate the operating portions 45p of independent displacement filaments 45 proximally, the loops formed in the filaments 45 around the corresponding ligating band 35 advance distally and slide the ligating band 35 over the surface 28 to the distal edge 29 as shown in FIG. 8. Additional proximal translation of the filament proximal portions 45p shift the ligating band 35 off the distal edge 29 causing the ligating band to collapse to the position shown in phantom in FIG. 8. At the same time the filament distal portions 45d disengage and separate from the ligating band 35 because of the ends 85 and adjacent distal portions 45d fall out of the notches 65a and 75a. Thereafter continued proximal displacement of the filaments 45 removes these filaments from the dispenser 22 and the endoscope 21.

Figure 9:
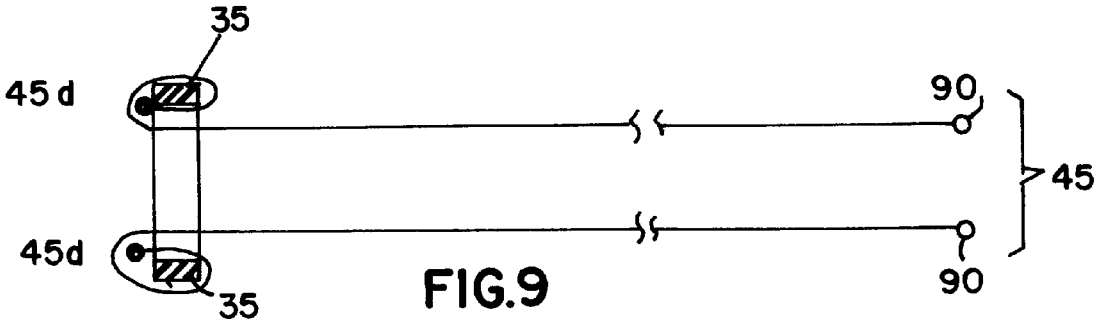
FIG. 9 depicts, in schematic form, the elements that extend between the distal and proximal ends of the dispenser shown in FIG. 1.

FIG. 9 schematically depicts the interconnection of the independent displacement means in the form of the distal portions 45d of the filaments 45 and the operator portions 45p. In this particular embodiment each operator portion 45p comprises a finger loop 90 that enables a physician to grasp the proximal portions 45p and displace the filaments 45 proximally. In a six-band dispenser, twelve filaments and loops emerge from the proximal end of the endoscope 21.

Figure 10:
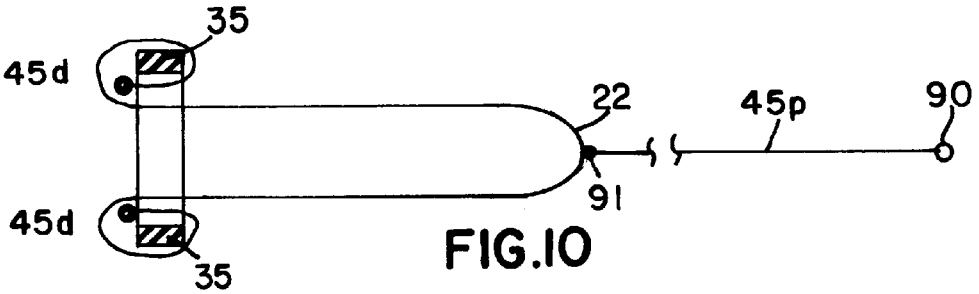
FIGS. 10 and 11 depict alternative embodiments of the elements shown in FIG. 9.

FIG. 10 discloses an alternative structure in which a single loop 90 is formed in a single filament operating portion 45p that connects internally of the endoscope 21 to both independent displacement filaments 45d at a junction 91. In a six-band dispenser, six loops 90 and attached proximal portions 45p emerge from the proximal end of the endoscope 21.

Figure 11:
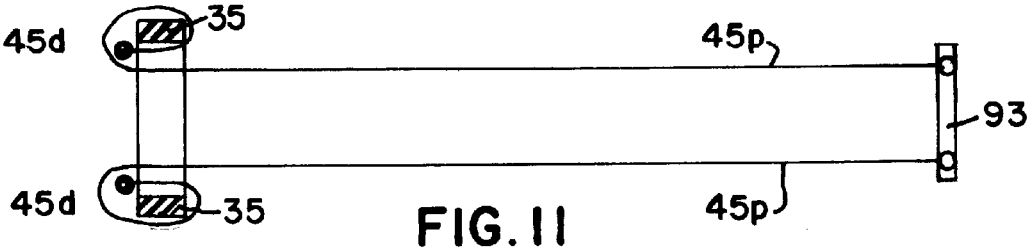

FIG. 11 discloses still another embodiment in which the operator filament proximal portions 45p connect to a single handle 93. When the physician pulls the handle 92, the operating portion 45p displaces the ligating band 35 distally. In a six-band dispenser, six handles 93 and proximal portions 45p emerge from the proximal end of the endoscope 21. As an alternative the handle 93 might connect to a single filament or pair of filaments that connect to each of the distal filament portions 40d through 45d in such a way that continuous proximal motion of the handle 93 displaces the ligating bands in sequence.

Thus, it will be apparent that the disclosed apparatus constitutes a dispenser for the sequential application of multiple ligating bands to diverse lesions. This occurs without requiring removal of the ligating band dispenser and introducer from a patient after each ligation. In the particular embodiment of FIG. 1 the dispenser 22 carries six ligating bands. Other dispensers could be constructed to carry other numbers of ligating bands. The maximum number of bands tends to be dictated by the maximum dispenser length that can be introduced into the patient. It will also be apparent that the support 26, connector 27, ligating bands 30 through 35 and corresponding filaments 40 through 45 will be packaged as a single unit for attachment to either a rigid or flexible endoscope or other introducer with the filaments 40 through 45 being drawn through the a working channel using conventional techniques. The ligating instrument comprises no moving parts; it is mechanically reliable. The only operating requirement is to select the most distal set of filaments at the proximal end of the endoscope and pull those elements first. This selection can be made by viewing labels, by color coding tags, by encoding filament length or other means. Thus, the ligating band dispenser utilizing this invention is easy to use. Moreover, the forces acting on the ligating bands during the introduction of the dispenser tend to move the ligating bands proximally, and not distally. The structure also minimizes any possibility of premature ejection of a ligating band. The elimination of a moving inner tube, as present in the prior art as the most distal element, further minimizes the possibility that any seal formed between the distal edge of the ligating band dispenser and a lesion will be lost during a dispensing operation.

While this invention has been disclosed in terms of a particular embodiment and certain modifications thereto, it will be apparent that many other modifications can be made to the specifically disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A ligating band dispenser for attachment to the distal end of an endoscopic device further characterized by a proximal end and a lumen extending between the proximal and distal ends, said dispenser being adapted for supporting a given plurality of elastic ligating bands and comprising:

A. support means for attachment to the distal end of the endoscopic device and for carrying the given plurality of ligating bands thereon, said support means having a passage therethrough for communication with the lumen, and B. dispensing means including:

i. a plurality of independent displacement means corresponding to the given plurality extending into the lumen of the endoscopic device, each said displacement means being attached to said support means and engaging a corresponding one of the ligating bands, and ii. operator means extending from each of independent displacement means through the lumen of the endoscopic device thereby to be accessible at the proximal end thereof whereby proximal motion of said operator means from the proximal end of the endoscopic device transfers the most distal ligating band off the distal end of said support means.

2. A ligating band dispenser as recited in claim 1 wherein said support means includes tubular body means having an exterior cylindrical surface for carrying the ligating bands and having a proximal shoulder portion and includes connector means for connecting said shoulder portion to the proximal end of the endoscope.

3. A ligating band dispenser as recited in claim 1 wherein each of said plurality of independent displacement means includes a plurality of filaments having the distal end attached to a corresponding one of the ligating bands.

4. A ligating band dispenser as recited in claim 3 wherein said support means includes a distal edge portion and wherein each of said plurality of filaments extends distally of said distal edge portion from a corresponding one of said operator means, loops around a corresponding ligating band and releasably attaches to said support means at said distal edge portion.

5. A ligating band dispenser as recited in claim 4 wherein each said filament lies intermediate said support means and all ligating bands intermediate the corresponding ligating band and said distal edge portion.

6. A ligating band dispenser as recited in claim 4 wherein said filaments in each of said independent displacement means attach to said distal end and engage the corresponding ligating band substantially equiangularly.

7. A ligating band dispenser as recited in claim 4 wherein each of said independent displacement means comprises a pair of filaments that engage a corresponding ligating band and said distal edge portion at substantially diametrically opposed positions.

8. A ligating band dispenser as recited in claim 4 wherein each of said operator means comprises a grasping means formed in the proximal end of each said filaments for facilitating proximal displacement of said filaments and the corresponding ligating band from said dispenser.

9. A ligating band dispenser as recited in claim 4 wherein each of said operator means comprises a grasping means extending from the proximal end of the endoscope into said lumen and comprises bridle means for attaching said grasping means to the filaments in said corresponding independent displacement means for facilitating proximal displacement of said filaments and the corresponding ligating band from said dispenser.

10. A ligating band dispenser as recited in claim 4 wherein each of said operator means comprises a handle tied to the proximal end of each said filaments in a corresponding independent displacement means for facilitating proximal displacement of said filaments and the corresponding ligating band from said dispenser.

11. A ligating band dispenser as recited in claim 4 wherein said support means includes filament guide means located proximally of said distal edge portion for guiding said filaments proximally from said distal edge portion.

12. A ligating band dispenser as recited in claim 11 wherein said support means includes, proximally of said distal edge portion, a filament guide means for each of said plurality of filaments.

13. A ligating band dispenser as recited in claim 11 wherein said support means includes a filament guide means for directing each filament from the interior of said support means proximate said distal edge portion to the exterior of said support means over an intermediate portion thereof and to the interior of said support means at a proximal end thereof.

14. A ligating band dispenser as recited in claim 11 wherein each of said independent displacement means comprises a plurality of filaments at different angular positions for engaging a corresponding ligating band at spaced positions thereon and wherein a corresponding filament for each of said independent displacement means forms a filament group, said support means additionally including a filament group guide means for directing the filaments in each group from the distal to the proximal ends of said support means, each group of guide means at said distal end being spaced with respect to each other and being adjacent at said proximal end.

15. A ligating band dispenser as recited in claim 14 wherein each of said filament groups are substantially equiangularly displaced about said distal edge and wherein said guide means are grouped closely adjacent at said proximal end of said support means.

16. A ligating band dispenser as recited in claim 11 wherein each of said independent displacement means comprises a plurality of filaments at different angular positions for engaging a corresponding ligating band at spaced positions thereon and wherein a corresponding filament for each of said independent displacement means forms a filament group, said support means additionally including a filament group guide means for directing the filaments in each group from the distal to the proximal ends of said support means, each group of guide means at said distal end being spaced with respect to each other and said groups of guide means being adjacent at said proximal end.

17. A ligating band dispenser as recited in claim 16 wherein each of said groups are substantially equiangularly displaced about said distal edge and wherein said guide means are grouped closely adjacent at said proximal end of said support means.

*18. An apparatus for dispensing a flexible ligating band, wherein the device is coupleable to an endoscopic device having a distal end and a proximal end, the apparatus comprising:*

*a support member selectively coupleable to the distal end of the endoscopic device, wherein the support member includes an outer support surface adapted to receive at least one ligating band thereon; and*

*a filament which, when the device is in an operative configuration, extends from the proximal end of the endoscopic device to the support surface to engage a ligating band so that, when the filament is drawn proximally from the endoscopic device, a ligating band is released from the support surface.*

*19. An apparatus according to claim 18, wherein the filament includes a proximal portion coupled to a distal portion so that, when the device is in the operative configuration, the proximal portion extends from the proximal end of the endoscopic device to an intermediate location within the lumen and the distal portion extends from the intermediate location to the support surface, and wherein the distal portion includes a plurality of lines, each line extending to a corresponding location on the support surface.*

*20. An apparatus according to claim 18, wherein the support surface is substantially cylindrical and wherein the circumference of the support surface is selected so that it is greater than an unstretched diameter of the ligating bands which are flexible and are stretched to be placed on the support surface.*

*21. An apparatus according to claim 18, wherein the endoscope includes a lumen extending from the distal end to the proximal end thereof and wherein, when the support surface is coupled to the endoscope, the lumen communicates with a passage extending through the support surface and the filaments extend from the proximal end, through the lumen to the distal end, through the passage to the support surface.*

*22. An apparatus according to claim 18, wherein the support surface includes a guideway for receiving the filament therein so that the filament is maintained in a desired position on the support surface.*

*23. An apparatus for dispensing a plurality of ligating bands, wherein the apparatus is adapted to be coupled to an endoscopic device having a distal end and a proximal end, the apparatus comprising:*

*a support member selectively coupleable to the distal end of the endoscopic device, wherein the support member includes an outer support surface adapted to receive a plurality of ligating bands thereon; and*

*a plurality of filaments, each of which, when the device is in an operative configuration, contacts a respective ligating band so that, when each filament is drawn proximally, the respective ligating band is released from the support surface.*

*24. An apparatus according to claim 23, wherein the support surface includes a plurality of guideways, each of the guideways corresponding to a respective filament to maintain each filament in a desired position on the support surface.*

*25. A system for dispensing ligating bands comprising:*

*an endoscopic device having a distal end and a proximal end;*

*a support member coupled to the distal end of the endoscopic device, wherein the support member includes an outer support surface adapted to receive at least one ligating band thereon; and*

*a filament which, when the device is in an operative configuration, extends from the proximal end of the endoscopic device to the support surface to engage a ligating band so that, when the filament is drawn proximally from the endoscopic device, a ligating band is released from the support surface.*

*26. A system according to claim 25, wherein the endoscope includes a lumen extending therethrough from the proximal end to the distal end and wherein, when the support surface is coupled to the endoscopic device, the filament extends through the lumen to a passage extending through the support surface.*

*27. A system according to claim 25, wherein the ligating band is flexible and wherein an unstretched diameter of the ligating band is smaller than a diameter of the support surface.*

*28. A system according to claim 25, wherein the support surface is adapted to receive a plurality of ligating bands thereon.*

*29. A system for dispensing a ligating band comprising:*

*a support surface for holding a plurality of ligating bands thereon, the support surface being sized so that the ligating bands received thereon are stretched beyond an unstretched diameter, wherein, when the device is in a desired position inside a living body, the support surface is located adjacent to a portion of tissue to be ligated; and*

*a filament which, when the device is in the operative position, extends from a proximal end outside the living body to a distal end coupled to at least one ligating band received on the support surface so that, when the filament is pulled axially, the at least one ligating band is released from the support surface.*

*30. An apparatus according to claim 29, wherein the support surface includes at least one guideway for maintaining the filament in a desired position on the support surface.*

*31. The apparatus according to claim 30, wherein the at least one guideway includes a notch extending from a distal end of the support surface toward a proximal end thereof.*

*32. An apparatus for dispensing a plurality of flexible ligating bands to tissue within a living body, comprising:*

*a support member selectively coupled to a distal end of an endoscopic device, wherein the support member includes a passage therethrough and an outer support surface adapted to receive at least one ligating band thereon; and*

*at least one filament coupled to the at least one ligating band so that, when the at least one filament is drawn proximally, the at least one ligating band is released from the support surface.*

*33. An apparatus according to claim 32, wherein the support member is substantially cylindrical and includes at least one guiding notch formed in a distal end thereof and wherein the at least one filament is slidably received within the notch so that the filament is maintained at a desired location on the support surface.*

*34. An apparatus according to claim 32, wherein the support surface includes a passage therethrough and the filament extends therethrough.*

*35. An apparatus according to claim 32, wherein the ligating bands are flexible.*

*36. An apparatus according to claim 32, wherein the support surface is adapted to receive a plurality of ligating bands thereon.*

*37. A method for ligating tissue within a living body comprising the steps of:*

*positioning a support surface adjacent to a first portion of tissue to be ligated, wherein the support surface includes at least one ligating band received on an outer surface thereof and wherein a filament coupled to the at least one ligating band extends from the support surface to a proximal end;*

*drawing the tissue to be ligated into a passage extending through the support surface;*

*pulling the proximal end of the filament to release the at least one ligating band from the support surface so that the at least one ligating band encircles and grips the first portion of tissue.*

*38. A method according to claim 37, wherein the at least one ligating band includes a first ligating band and a second ligating band and wherein the first ligating band encircles and grips the first portion of tissue, further comprising the steps of:*

*positioning the support surface adjacent to a second portion of tissue to be ligated;*

*drawing the second portion of tissue into the passage; and*

*releasing the second ligating band so that the second ligating band encircles and grips the second portion of tissue.*

*39. A method according to claim 37, wherein the steps of drawing the first and second portions of tissue into the passage include the step of applying suction to the tissue via the passage.*

*40. A method according to claim 37, wherein the steps of positioning the support surface adjacent to the first portion of tissue includes the step of coupling the support surface to the distal end of an endoscope and guiding the endoscope through a body lumen so that the support surface is adjacent to the first portion of tissue.*

*41. An apparatus for ligating tissue within a living body comprising:*

*a support member for receiving a plurality of elastic ligating bands on a support surface thereof, wherein the support member includes means for selectively coupling to and decoupling from a distal end of an endoscopic device;*

*means for drawing tissue to be ligated into the support member; and*

*means for selectively releasing the ligating bands individually to encircle and elastically grip tissue received within the support member to cut off varices.*

* * * * *